United States Patent
Bracke et al.

(10) Patent No.: US 9,586,973 B2
(45) Date of Patent: Mar. 7, 2017

(54) HDAC6 INHIBITORS AND USES THEREOF

(71) Applicant: Universiteit Gent, Ghent (BE)

(72) Inventors: Marc Bracke, Wondelgem (BE); Matthias D'hooghe, Evergem (BE); Rob De Vreese, Ghent (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 14/858,350

(22) Filed: Sep. 18, 2015

(65) Prior Publication Data

US 2016/0009730 A1  Jan. 14, 2016

Related U.S. Application Data

(63) Continuation-in-part of application No. PCT/EP2014/055602, filed on Mar. 20, 2014.

(60) Provisional application No. 61/804,028, filed on Mar. 21, 2013.

(51) Int. Cl.
C07D 495/04 (2006.01)
A61K 31/407 (2006.01)
A61K 45/06 (2006.01)

(52) U.S. Cl.
CPC .......... *C07D 495/04* (2013.01); *A61K 31/407* (2013.01); *A61K 45/06* (2013.01)

(58) Field of Classification Search
None
See application file for complete search history.

(56) References Cited

FOREIGN PATENT DOCUMENTS

| WO | 2011/011186 A2 | 1/2011 |
|---|---|---|
| WO | WO2011/011186 | * 1/2011 |

OTHER PUBLICATIONS

Kaliszczak et al. in Britisih Journal of Cancer 108, 345-350 (2013).*
Remiszewski, S., et al., N-Hydroxy-3-phenl-2-propenamides as novel inhibitors of human histone deacetylase with in vivo antitumor activity: Discovery of (2E)-N-hydroxy-3-[4-[[2-hydroxyethyl) [2-(1H-indol-3-yl) ethyl]amino]methyl]phenyl]-3-propenamide (NVP-LAQ824), Journal of Medicinal Chemistry, American Chemical Society, vol. 46, 2003, pp. 4609-4624, XP002414496, U.S.A.
De Vreese, et al., Potent and selective HDAC6 inhibitory activity of N-(4-hydroxycarbamoylbenzyl)-1,2,4,9-tetrahydro-3-thia-9-azafluorenes as novel sulfur analogues of Tubastation A, The Royal Society of Chemistry, 2013, vol. 49, pp. 3775-3777, RSC Publishing, England.
International Search Report pertaining to Application No. PCT/EP2014/055602 with an International filing date of Mar. 20, 2014.
Written Opinion pertaining to Application No. PCT/EP2014/055602 with an International filing date of Mar. 20, 2014.

* cited by examiner

*Primary Examiner* — Dennis Heyer
(74) *Attorney, Agent, or Firm* — Dinsmore & Shohl LLP

(57) ABSTRACT

Histone deacetylases 6 (HDAC6) inhibitors and compositions containing the same. Methods of treating diseases and conditions wherein inhibition of HDAC6 provides a benefit, like a cell proliferative disease, an autoimmune or inflammatory disorder, a neurodegenerative disease, a viral disease, malaria, or a combination thereof.

14 Claims, 6 Drawing Sheets

US 9,586,973 B2

HDAC6 INHIBITORS AND USES THEREOF

CROSS-REFERENCE TO RELATED APPLICATIONS

This application is filed under 35 U.S.C. §111 as a continuation-in-part of International Patent Application No. PCT/EP2014/055602 (File Reference TTO-034), filed on Mar. 20, 2014, which designates the United States and claims priority to U.S. Provisional Application Ser. No. 61/804,028, filed on Mar. 21, 2013, the contents of which are hereby incorporated by reference in their entirety.

FIELD OF THE INVENTION

The present invention relates to Histone deacetylase 6 (HDAC6) inhibitors and compositions containing the same. Methods of treating diseases and conditions wherein inhibition of HDAC6 provides a benefit, like a cell proliferative disease, an autoimmune or inflammatory disorder, a neurodegenerative disease, a viral disease, malaria, or a combination thereof, also are disclosed.

BACKGROUND OF THE INVENTION

The enzymatic addition and removal of acetyl groups at specific lysine residues comprise important biochemical reactions with a significant impact on many cellular processes.[1] The addition of acetyl groups within histone proteins, the chief protein components of chromatin, is catalyzed by histone acetyltransferases (HAT), and histone deacetylases (HDAC) mediate the corresponding deacetylation reactions. The inhibition of the latter group of deacetylases has become a hot topic in medicinal chemistry, and the use of HDAC inhibitors (HDACIs) has found many applications with regard to cancer and CNS disorder therapies.[2] In general, HDACIs act on 11 zinc-dependent HDAC isozymes, which are divided into four groups: class I (HDACs 1, 2, 3, 8), class IIa (HDACs 4, 5, 7, 9), class IIb (HDACs 6, 10), and class IV (HDAC11).[3] The majority of known HDACIs primarily inhibit the class I enzymes, making them excellent candidates for cancer therapy applications, but other than class I HDACIs are normally required for the pursuit of non-oncology applications.[4] Another important issue relates to the potential toxicity of compounds inhibiting multiple isozymes, as acetylation is involved in the control of many cellular processes and inhibition of some isozymes may cause undesirable side effects. Thus, the design and development of isozyme-selective inhibitors has emerged as an important challenge within the search for novel HDACIs.[5]

In recent years, HDAC6 has been acknowledged as an attractive target for drug development,[6] and an increasing number of research teams are currently involved in the quest for new compounds endowed with HDAC6 inhibitory activity.[7] HDAC6 is a Zn dependent (1216aa) Class IIb HDAC isoform that de-acetylates cytoplasmic (non-histone) substrates—primarily tubulin, cortactin (actin network) and Hsp90. In addition to the potential of HDAC6-selective inhibitors for applications in the treatment of CNS disorders and neurodegenerative diseases, these compounds seem to provoke less side effects, hence the growing interest in their preparation.[8] An important milestone in that respect concerns the identification of Tubacin as a selective HDAC6 inhibitor, although the application of this compound is hampered by its poor druglikeness and cumbrous synthesis.[9] Since then, considerable advances have been made with regard to the preparation of new HDAC6 inhibitors, leading to an array of different molecular entities with improved chemical and pharmacological properties.[7] From a chemical viewpoint, many of these molecules comprise the typical HDACI basic structure accommodating an aromatic cap group (surface recognition domain), a linker and a zinc-binding hydroxamic acid unit. A major breakthrough was accomplished recently, involving the rational design and synthesis of Tubastatin A as a novel and selective HDAC6 inhibitor.[10] A later study by Kahn and coworkers observed that substitutions on the tetrahydrocarboline group of Tubastatin A analogues influence HDAC6 activity and selectivity.[11]

Despite these promising results, the structural requirements for selective inhibition remain largely unknown. Some compounds have been reported to display relative HDAC6 selectivity or preferential HDAC6 inhibition. Despite much effort, truly selective compounds are few, and the precise structural determinants required to achieve the selective inhibition of single HDAC isozymes generally remain undefined.

There is thus still a need in the art for novel HDACIs, and particularly selective HDAC6 inhibitors, that are useful in the treatment of diseases wherein HDAC inhibition provides a benefit, such as a cell proliferative disease, an autoimmune or inflammatory disorder, a neurodegenerative disease, a viral disease, malaria, or a combination thereof (see also WO2011011186 for an overview of diseases treatable with HDAC6 inhibitors). Accordingly, a significant need exists in the art for efficacious compounds, compositions, and methods useful in the treatment of such diseases, alone or in conjunction with other therapies used to treat these diseases and conditions. The present invention is directed to meeting this need.

DETAILED DESCRIPTION

Figure 1A:
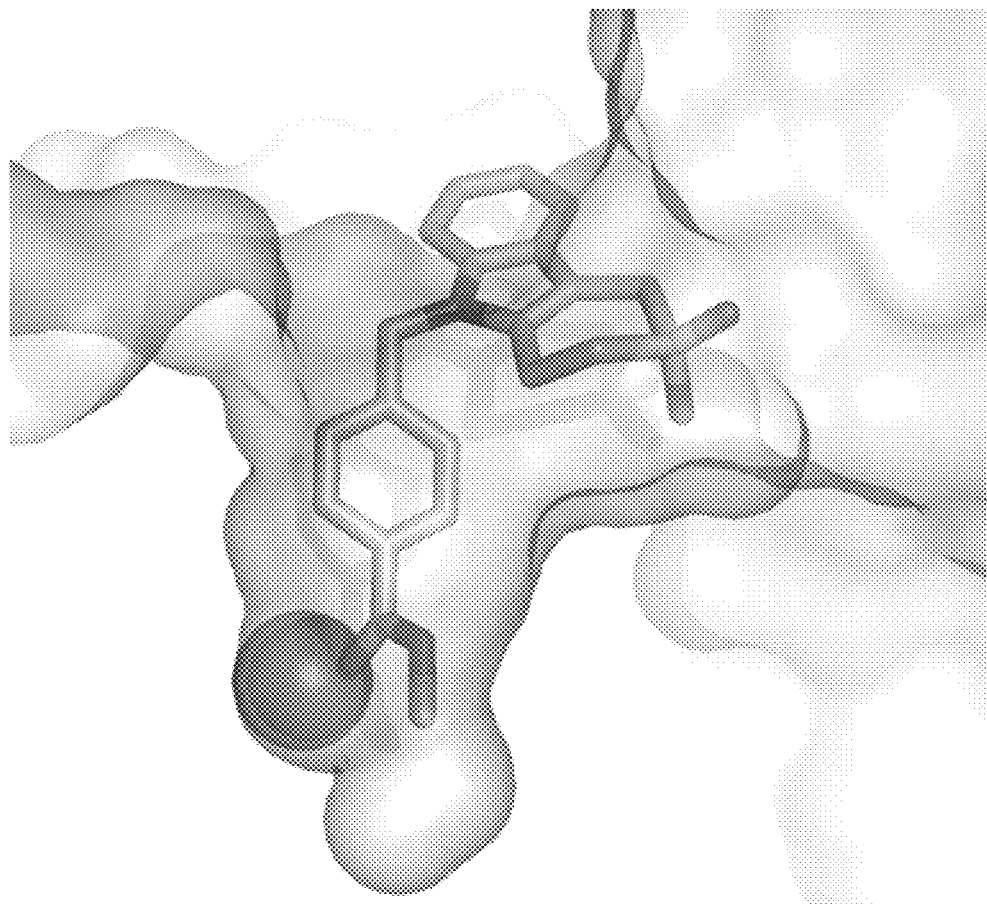
FIG. 1A: Depicts a view of the tubular access channel in docking of compound 10A in the active site of HDAC6.

Despite the therapeutic advantage of isoform-selective HDAC inhibitors, design of such inhibitors has been challenging due to the high sequence similarity within the active sites of the isoforms. The present invention provides inhibitors that are structurally distinct from known HDAC inhibitors and that are highly selective toward the HDAC6 isoform.

The present invention relates to compounds having the Formulas as disclosed herein, including derivatives, prodrugs and pharmaceutically acceptable salts thereof, compositions and kits comprising such compounds, methods for making, and methods of use in treating histone deacetylase-associated disorders.

Structures of Tubacin (1) and Tubastatin A (2)

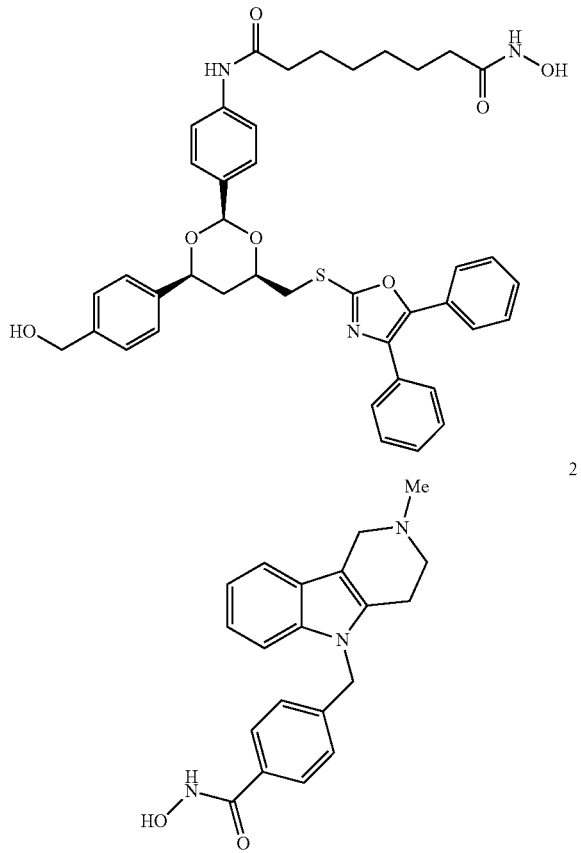

While Tubastatin A and its prior art analogues invariantly have a tetrahydro-carboline cap group, the inventors of the present application have surprisingly found that analogues comprising a tetrahydro-thia-azafluorene cap group, or their sulfone analogues, also display strong HDAC6 inhibition. The results obtained show the potential of these sulfur analogues of Tubastatin A as new HDAC6 inhibitors, especially those containing a sulfone moiety in their structure. Even more surprisingly, these analogues show a much higher selectivity for HDAC6 compared to Tubastatin A and are also potent. The in silico observed occurrence of hydrogen bonds between the introduced oxygen atoms and the backbone nitrogen atom of residues Asp567 and Gly619 can account for the higher in vitro activity of these sulfone derivatives. Moreover, these compounds can be synthesized in only a few steps which is attractive for scaling up and industrial synthesis.

In a first embodiment, the invention provides a compound of formula I, or a stereoisomer, tautomer, racemic, metabolite, pro- or predrug, salt, hydrate, or solvate thereof:

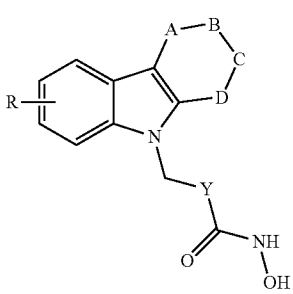

wherein:
ring

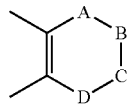

is a five- or six-membered ring wherein one of A, B, C and D is S, S=O, or $SO_2$ and the remaining are a direct bond or $CH_2$;

Y is selected from alkylene, cycloalkylene, heterocyclylene, arylene, and heteroarylene;

R is selected from the group consisting of hydrogen, halogen, alkyl, haloalkyl, cycloalkyl, heterocyclyl, aryl, heteroaryl, OR', SR', NR'R", and P(O)(OR')(OR"); and R' and R" are independently selected from the group consisting of H, alkyl, and aryl.

The term "halogen" refers to an element selected from the group consisting of fluorine (F), chlorine (Cl), bromine (Br), iodine (I), and astatine (At).

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms, preferably from 1 to 6 carbon atoms. Alkyl groups may be linear or branched. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl (also shortened as Me), ethyl, n-propyl (also shortened as nPr), i-propyl (also shortened as iPr), butyl, and its isomers (e.g. n-butyl, i-butyl (also shortened as iBu) and t-butyl (also shortened as tBu)); pentyl and its isomers, hexyl and its isomers, heptyl and its isomers, octyl and its isomers, nonyl and its isomers; decyl and its isomers.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "cycloalkyl" by itself or as part of another substituent is a cyclic alkyl group, that is to say, a monovalent, saturated, or unsaturated hydrocarbyl group having 1, 2, or 3 cyclic structure. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Preferred are monocyclic cyloalkyl groups, comprising a single ring. Examples of monocyclic cycloalkyl groups include but are not limited to cyclopropyl, cyclobutyl, cyclopentyl, cyclohexyl, cycloheptyl, cyclooctyl, cyclononyl, and cyclodecyl with cyclopropyl, cyclopentyl, cyclohexyl, and cycloheptyl being particularly preferred. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

The term "heterocyclyl" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. Preferred heterocyclyls are monocyclic heterocyclic groups, in particular 4 to 7 membered monocyclic groups containing 1 or 2 heteroatoms.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

The term "aryl" as used herein refers to a polyunsaturated, aromatic hydrocarbyl group having a single ring (i.e. phenyl (also shortened as Ph)) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl. Preferred aryl groups have a single ring, such as phenyl.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d] [1,3] thiazolyl, thieno [2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl. Preferred heteroaryls include monocylic heteroaryl groups, in particular 4 to 7 membered monocyclic groups containing 1 or 2 heteroatoms.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, an arylene group refers to a bivalent group derived from an arene by removal of a hydrogen atom from each of two ring carbon atoms. A synonym is arenediyl group. A preferred group is phenylene, in particular meta- or para-phenylene. Meta-phenylene as used herein refers to a divalent benzene group, wherein the two single bonds for attachment to other groups are located in the meta-position of each other. Similarly, para-phenylene refers to a benzene group having two single bonds in the para-position of each other.

In another embodiment, the invention provides a compound of formula I, or a stereoisomer, tautomer, racemic, metabolite, pro- or predrug, salt, hydrate, or solvate thereof:

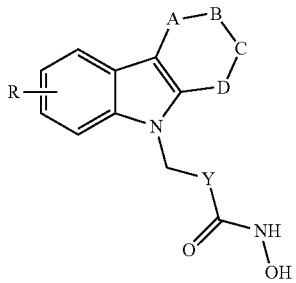

I wherein:
ring

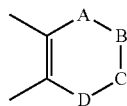

is a five- or six-membered ring containing one $SO_2$— or one S-group,

A, B, C and D are selected from the group consisting of a direct bond, $CH_2$, S and $SO_2$, Y is selected from the group alkylene or arylene, and R is absent, a halogen or is selected from the group consisting of: Me, Pr, iPr, iBu, tBu, $CF_3$, Ph, aryl, OR', SR', NR'$_2$, and P(0)(OR')$_2$ (with R'=H, alkyl or aryl).

In a particular embodiment, the present invention provides compounds of formula I wherein
ring

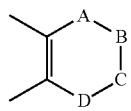

is a five- or six-membered ring wherein one of A, B, C and D is $SO_2$ and the remaining are a direct bond or $CH_2$.

In another particular embodiment, the present invention provides compounds of formula I wherein
ring

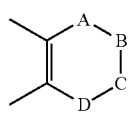

is a five- or six-membered ring wherein one of A, B, C and D is S and the remaining are a direct bond or $CH_2$.

In another particular embodiment, the present invention provides compounds of formula I wherein
ring

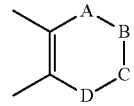

is a five- or six-membered ring wherein one of A, B, C and D is S, SO or $SO_2$ and the remaining are a direct bond or $CH_2$.

In a preferred embodiment, the present invention provides those compounds of formula I, wherein
A is a direct bond or $CH_2$;
B is selected from the group consisting of S, S=O, and $SO_2$; and
C and D are $CH_2$.

In another preferred embodiment, the present invention provides those compounds of formula I, wherein
A is a direct bond or $CH_2$;
B is selected from the group consisting of S, S=O, and $SO_2$; in particular from S and $SO_2$;
C and D are $CH_2$;
Y is arylene; in particular phenylene;
R is selected from the group consisting of hydrogen, halogen, alkyl, haloalkyl, OR', SR', NR'R", and P(O)(OR')(OR"); and
R' and R" are independently selected from the group consisting of H, alkyl, and aryl.

In a particular embodiment, R is selected from the group consisting of hydrogen, halogen, alkyl, haloalkyl, cycloalkyl, heterocyclyl, aryl, heteroaryl, OR', SR', NR'R", and P(O)(OR')(OR"); in particular from hydrogen, halogen, alkyl, haloalkyl, aryl, OR', SR', NR'R", and P(O)(OR')(OR"); more in particular from Me, Pr, iPr, iBu, tBu, $CF_3$, Ph, aryl, OR', SR', NR'$_2$, and P(O)(OR')$_2$ (with R'=H, alkyl or aryl). In a further embodiment, the present invention provides those compounds as described herein, wherein R is selected from hydrogen, halogen, and aryl; in particular from hydrogen, halogen and phenyl; more in particular from hydrogen and halogen. In yet another particular embodiment, the present invention provides compounds of formula I as described herein, wherein none of A, B, C and D is a direct bond.

In a particular

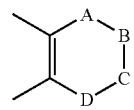

is a six membered ring.

In yet another embodiment, the present invention provides those compounds of formula I as described herein wherein
Y is alkylene or arylene; in particular Y is phenyl or a $C_{3-13}$ alkylene; in particular Y is phenyl or a $C_{3-9}$ alkylene; In another embodiment Y is phenyl;
R is selected from the group consisting of hydrogen, halogen, $C_{1-8}$alkyl, aryl, OR', SR', NR'R", P(O)(OR')(OR"), and $C_{1-8}$alkyl substituted with halo; and
R' and R" are independently selected from the group consisting of H, alkyl, and aryl. In a further embodiment, R' and R" are selected from H and $C_{1-6}$alkyl; in particular H. In another embodiment, R' and R" are identical.

In a preferred embodiment, R is selected from the group consisting of hydrogen, halogen, $C_{1-8}$alkyl, and $C_{1-8}$alkyl substituted with halo; in particular hydrogen or halogen; more in particular halogen. Preferred halogens for R are bromo or fluoro. Therefore, in a particular embodiment, the present invention provides compounds of formula I wherein R is selected from hydrogen, bromo, and fluoro. In a further preferred embodiment, R is fluoro. In another embodiment, R is bromo.

In another particular embodiment, the present invention provides those compounds of formula I as described herein, wherein Y is para-phenylene, meta-phenylene, or alkyl; in particular para-phenylene or meta-phenylene; more in particular para-phenylene.

In a further embodiment, the invention provides a compound having one of the formulas II-VI, wherein R is as defined herein:

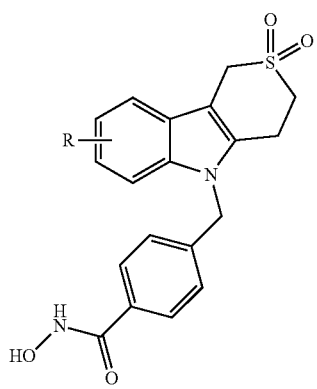

II

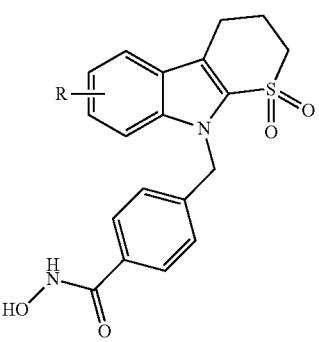

III

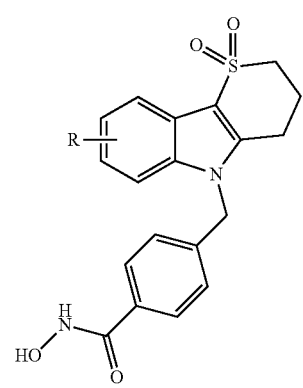

IV

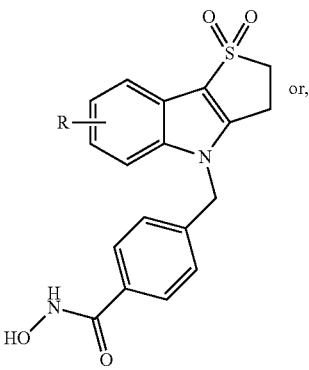

V

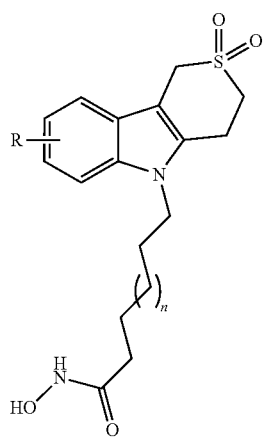

VI

Wherein n is an integer of 0 to 10; in particular n is an integer of 0 to 6.

In a further particular embodiment, the present invention provides a compound of Formula II; in particular a compound of Formula II wherein R is selected from hydrogen, bromo, and fluoro; more in particular wherein R is bromo.

In a further embodiment, the invention provides a compound selected from the group consisting of:

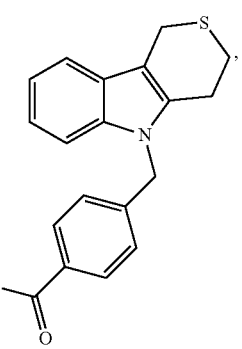

11
-continued
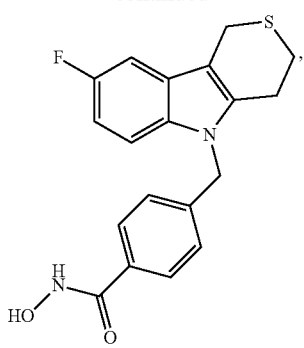
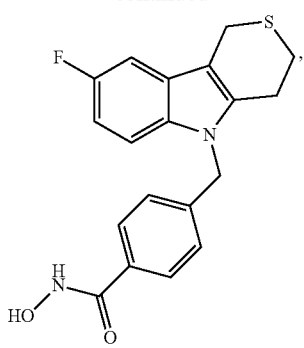
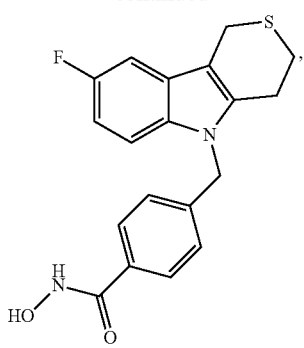
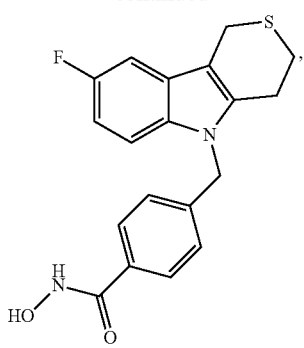
12
-continued
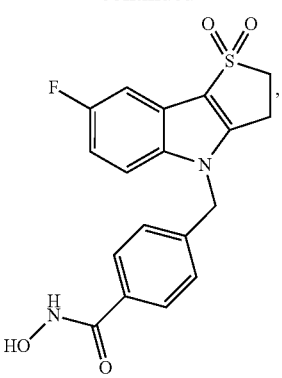
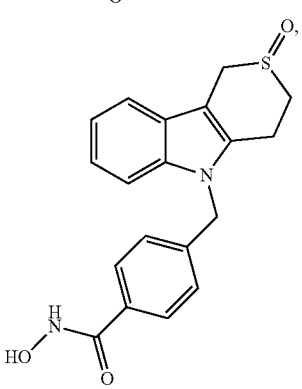
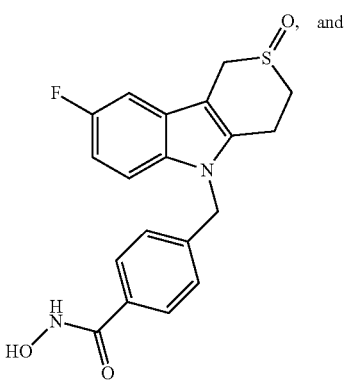
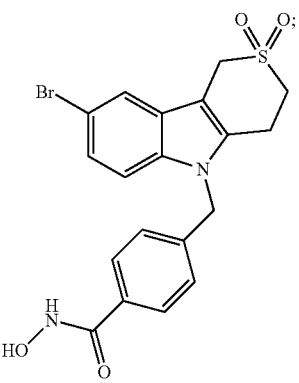

in particular from the group consisting of

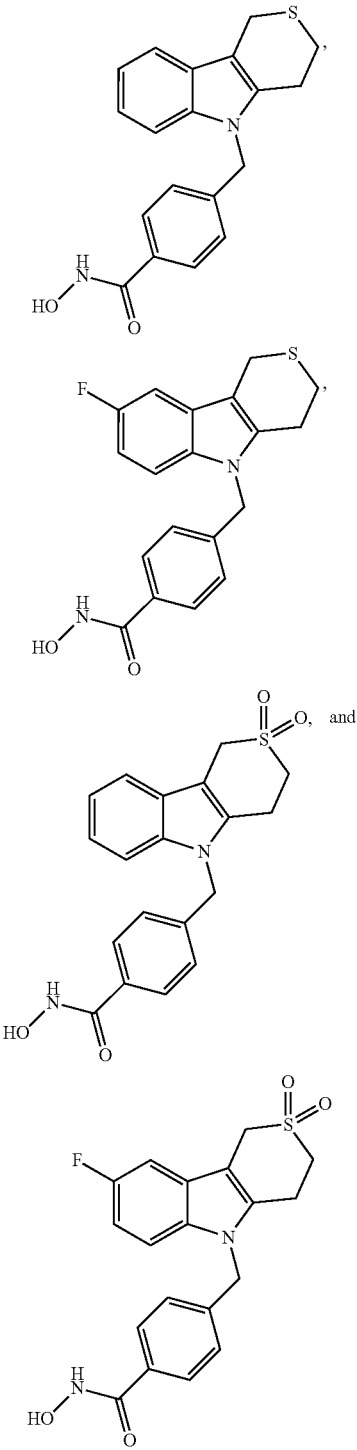

or a stereoisomer, tautomer, racemic, metabolite, pro- or predrug, salt, hydrate, or solvate thereof.

In a particular embodiment the present invention provides a compound of formula I for use as a medicine, in particular a human or veterinary medicine. In a further embodiment, the present invention provides a composition comprising a compound as described herein. The composition may be a pharmaceutical composition comprising a compound of the invention and one or more pharmaceutically acceptable carriers or excipients.

In a particular embodiment, the present invention provides a compound of formula I for use in the treatment and/or prevention of a HDAC-associated disease, in particular a HDAC6-associated disease.

As used herein, the terms "treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated, including the treatment of acute or chronic signs, symptoms and/or malfunctions. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. The term "treat" and synonyms contemplate administering a therapeutically effective amount of a compound of the invention to an individual in need of such treatment. A treatment can be orientated symptomatically, for example, to suppress symptoms. It can be effected over a short period, be oriented over a medium term, or can be a long-term treatment, for example within the context of a maintenance therapy.

In a further embodiment the invention relates to the use of compounds of the invention in a method of treating a histone deacetylase (HDAC)-associated disease, comprising: (a) providing at least one compound of Formula I-VI as described herein; and (b) administering a composition to a subject with symptoms of the HDAC-associated disease, comprising a therapeutic amount of the HDAC inhibitor compound and a pharmaceutically acceptable carrier, wherein the therapeutic amount is effective to inhibit the activity of at least the HDAC6 isoform and in treating the symptoms of the HDAC-associated disease. A HDAC(6)-associated disease is characterized by lower level of acetylated tubulin in cells isolated from the subject with symptoms of the HDAC-associated disease relative to the level of acetylated tubulin in cells isolated from a healthy subject. More specific, the HDAC-associated disease is selected from the group consisting of a cell proliferative disease, an autoimmune or inflammatory disorder, a neurodegenerative disease, a viral disease, malaria, or a combination thereof. In a further embodiment, the HDAC-associated disease is selected from the group consisting of a cell proliferative disease, an autoimmune or inflammatory disorder, a neurodegenerative disease, or a combination thereof.

In a particular embodiment, the HDAC-associated disease is a cell proliferative disease. According to another embodiment, the cell proliferative disease is a cancer, in particular metastasis thereof, selected from the group consisting of an ovarian cancer, a prostate cancer, a lung cancer, an acute myeloid leukemia, a multiple myeloma, a bladder carcinoma, a renal carcinoma, a breast carcinoma, a colorectal carcinoma, a neuroblastoma, a melanoma, a gastric cancer, or a combination thereof. According to another embodiment, the autoimmune or inflammatory disorder is selected from the group consisting of a rheumatoid arthritis, a psoriasis, an inflammatory bowel disease, a multiple sclerosis, a systemic lupus erythematosus, an airway hyperresponsiveness, a Crohn's disease, an ulcerative colitis, or a combination thereof. In another particular embodiment, the present invention provides a method for inhibiting the proliferation of cells, in particular inhibiting tumor growth, said method comprising administering a compound of the invention to a subject. In a preferred embodiment, the cancer is a solid tumor cancer.

According to another embodiment, the neurodegenerative disorder is selected from the group consisting of a cerebral ischemia, a Huntington's disease, an amyotrophic lateral sclerosis, a spinal musclular atrophy, a Parkinson's disease, an Alzheimer's disease, a peripheral nervous system disorder and other hereditary axonopathies, or a combination thereof.

According to another embodiment, the HDAC-associated disease is an inflammatory disease, such as arthritis, in particular rheumatoid arthritis.

The present methods also encompass administering a second therapeutic agent to the individual in addition to a compound of the invention. The second therapeutic agent is selected from agents, such as drugs and adjuvants, known as useful in treating the disease or condition afflicting the individual, such as a cell proliferative disease, an autoimmune or inflammatory disorder, and/or a neurodegenerative disease.

For example a chemotherapeutic agent and/or radiation known as useful in treating a particular cancer. The present invention includes methods for treating cancer comprising administering to an individual in need thereof a compound according to the invention and one or more additional anticancer agents or pharmaceutically acceptable salts thereof. The compound of the invention and the additional anticancer agent can act additively or synergistically. Suitable anticancer agents include, but are not limited to, gemcitabine, capecitabine, methotrexate, taxol, taxotere, mereaptopurine, thioguanine, hydroxyurea, cyclophosphamide, ifosfamide, nitrosoureas, mitomycin, dacarbazine, procarbizine, etoposide, teniposide, campatheeins, bleomycin, doxorubicin, idarubicin, daunorubicin, dactinomycin, plicamycin, mitoxantrone, L-asparaginase, doxorubicin, epirubicin, 5-fluorouracil (5-FU), taxanes (such as docetaxel and paclitaxel), leucovorin, levamisole, irinotecan, estramustine, etoposide, nitrogen mustards, BCNU, nitrosoureas (such as carmustine and lomustine), platinum complexes (such as cisplatin, carboplatin and oxaliplatin), imatinib mesylate, hexamethylmelamine, topotecan, tyrosine kinase inhibitors, tyrphostins herbimycin A, genistein, erbstatin, and lavendustin A.

As used herein a subject is a human or animal, in particular human.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc.

The invention will now be illustrated by means of the following examples, which do not limit the scope of the invention in any way.

Examples

Synthesis

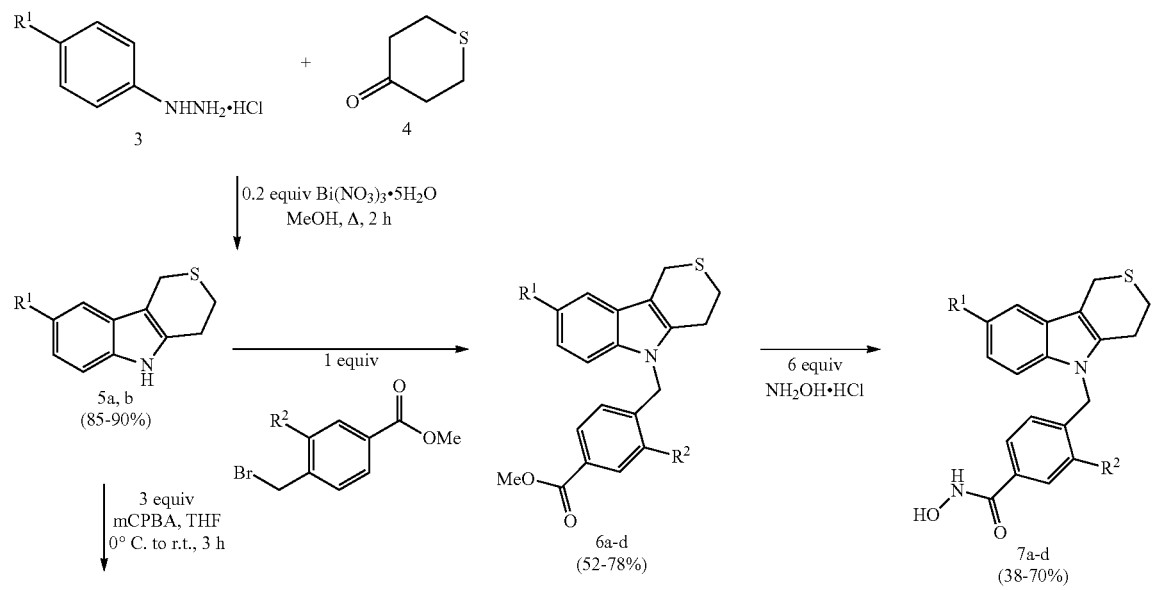

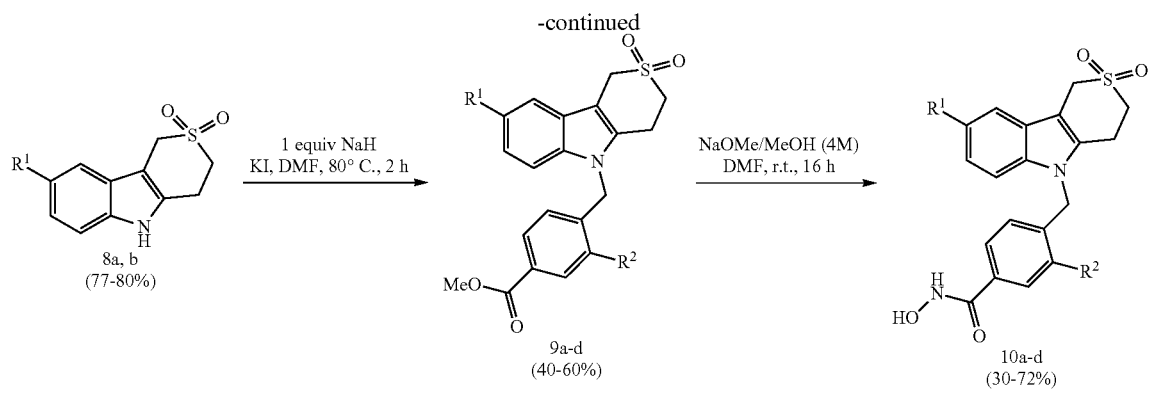

a) General Procedure For The Preparation Of 1,2,4,9-tetrahydro-3-thia-9-azafluorenes 5

To a solution of phenyl hydrazine hydrochloride 3 (12 mmol) and tetrahydrothiopyran-4-one 4 (12 mmol) in methanol (50 mL) was added Bi(NO₃)₃·5H₂O (2.4 mmol). After being stirred for 2 h under reflux, the reaction mixture was poured into water (100 mL), and bismuth nitrate was removed trough filtration. The crude product was extracted with ethyl acetate (100 mL), washed with saturated NaHCO₃ (100 mL), brine (100 mL) and dried over anhydrous MgSO₄. Filtration of the drying agent and removal of the solvent in vacuo afforded the crude thioether 5, which was purified by means of recrystallization from ethanol to provide pure 1,2,4,9-tetrahydro-3-thia-9-azafluorene 5 (10.2 mmol, 85%).

b) General Procedure For The Preparation Of Sulfones 8

To a solution of 1,2,4,9-tetrahydro-3-thia-9-azafluorene 5 (5 mmol) in tetrahydrofuran (50 mL) was added m-chloroperbenzoic acid in tetrahydrofuran (>70%, 15 mmol) at 0° C. The mixture was stirred at room temperature for 2 h. The solvent was removed in vacuo and the residue was dissolved in ethyl acetate (100 mL). The solution was washed with saturated aqueous sodium sulfite (30 mL), water (30 mL), brine (2×30 mL), and dried over anhydrous MgSO₄. Filtration of the drying agent and removal of the solvent in vacuo afforded the crude sulfone 8, which was purified by recrystallization from EtOH to provide pure 1,2,4,9-tetrahydro-3-thia-9-azafluorene-3,3-dioxide 8 (3.85 mmol, 77%).

c) General Procedure For The Preparation Of Esters 6 and 9

1,2,4,9-Tetrahydro-3-thia-9-azafluorene 5 (6 mmol) and sodium hydride (60 wt % in mineral oil, 6 mmol) were placed under nitrogen and dissolved in DMF (10 mL). After stifling for 30 minutes, methyl 4-(bromomethyl)benzoate (6 mmol) and potassium iodide (10 mg) were added to the reaction. The reaction was heated to 80° C. for 2 h, after which the reaction was quenched with water (30 mL) followed by addition of ethyl acetate (30 mL). The aqueous layer was extracted with ethyl acetate (2×10 mL) and the combined organic layers were washed with water (2×20 mL), brine (15 mL), dried (MgSO₄) and concentrated in vacuo. Recrystallization from ethanol afforded pure N-(4-methoxycarbonylbenzyl)-1,2,4,9-tetrahydro-3-thia-9-azafluorene 6 (3.12 mmol, 52%).

d) General Procedure For The Preparation Of Hydroxamic Acids 7 and 10

To a solution of ester 6 (0.6 mmol) and hydroxylamine hydrochloride (3.6 mmol) in DMF (5 mL) under nitrogen atmosphere was added NaOMe/MeOH (4M, 1.2 mL, 4.8 mmol). The reaction was stirred for 16 h at room temperature and a white precipitate was formed. The reaction mixture was diluted with ethyl acetate (20 mL) and extracted with saturated NaHCO₃ (10 mL), brine (2×10 mL), and dried with anhydrous MgSO₄. Filtration of the drying agent and removal of the solvent in vacuo afforded the crude hydroxamic acid 7, which was recrystallized from ethanol to afford pure N-(4-hydroxycarbamoylbenzyl)-1,2,4,9-tetrahydro-3-thia-9-azafluorene 7 (0.23 mmol, 38%).

TABLE 1

| Entry | R¹ | R² | Compound (yield)[a] |
|---|---|---|---|
| 1 | H | — | 5a (85%) |
| 2 | F | — | 5b (90%) |
| 3 | H | H | 6a (52%) |
| 4 | H | MeO | 6b (57%) |
| 5 | F | H | 6c (69%) |
| 6 | F | MeO | 6d (78%) |
| 7 | H | H | 7a (38%) |
| 8 | H | MeO | 7b (65%) |
| 9 | F | H | 7c (70%) |
| 10 | F | MeO | 7d (66%) |
| 11 | H | — | 8a (77%) |
| 12 | F | — | 8b (80%) |
| 13 | H | H | 9a (48%) |
| 14 | H | MeO | 9b (60%) |
| 15 | F | H | 9c (47%) |
| 16 | F | MeO | 9d (40%) |
| 17 | H | H | 10a (51%) |
| 18 | H | MeO | 10b (30%) |
| 19 | F | H | 10c (69%) |
| 20 | F | MeO | 10d (72%) |

[a]Yields after purification by column chromatography (SiO₂) or recrystallization Similarly to the above, the following compounds of the invention were made:

| Structure | Compound |
|---|---|
| 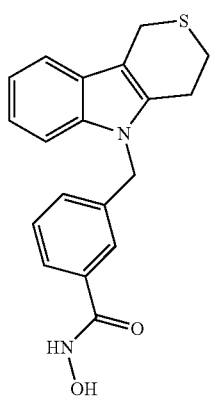 [SMILES: O=C(NO)c1cccc(Cn2c3c(c4ccccc42)CSCC3)c1] | 11 |
| 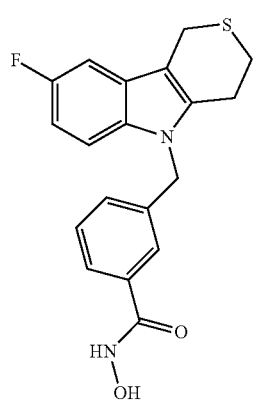 [SMILES: O=C(NO)c1cccc(Cn2c3c(c4cc(F)ccc42)CSCC3)c1] | 12 |
| 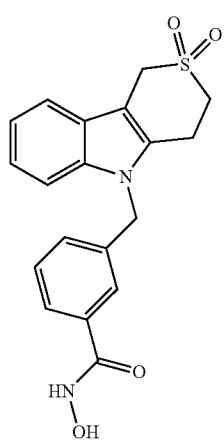 [SMILES: O=C(NO)c1cccc(Cn2c3c(c4ccccc42)CS(=O)(=O)CC3)c1] | 13 |
-continued
| Structure | Compound |
|---|---|
| 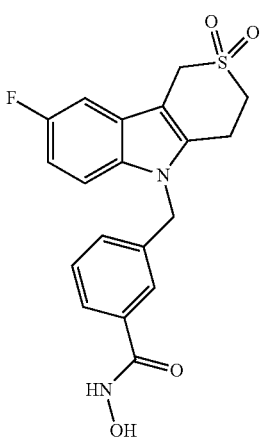 [SMILES: O=C(NO)c1cccc(Cn2c3c(c4cc(F)ccc42)CS(=O)(=O)CC3)c1] | 14 |
| 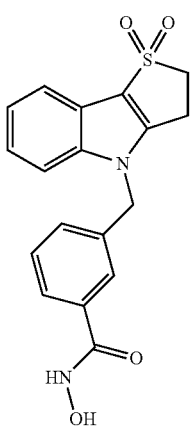 [SMILES: O=C(NO)c1cccc(Cn2c3c(c4ccccc42)S(=O)(=O)CC3)c1] | 15 |
| 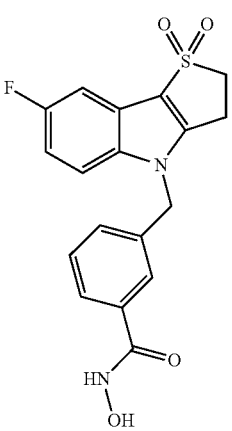 [SMILES: O=C(NO)c1cccc(Cn2c3c(c4cc(F)ccc42)S(=O)(=O)CC3)c1] | 16 |

| Structure | Compound |
|---|---|
| (structure) | 17 |
| (structure) | 18 |

Other exemplary compounds of the invention include:

| Structure | Compound |
|---|---|
| (structure) | 19 |
| (structure) | 20 |
| (structure) | 21 |
| (structure) | 22 |
| (structure) | 23 |

-continued

| Structure | Compound |
|---|---|
| (structure) | 24 |
| (structure) | 25 |
| (structure) | 26 |
| (structure) | 27 |

-continued

| Structure | Compound |
|---|---|
| (structure) | 28 |
| (structure) | 29 |
| (structure) | 30 |
| (structure) | 31 |

| Structure | Compound |
|---|---|
| 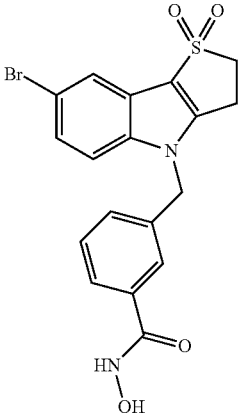 [SMILES: O=C(NO)c1cccc(Cn2c3c(c4cc(Br)ccc42)S(=O)(=O)CC3)c1] | 32 |
| 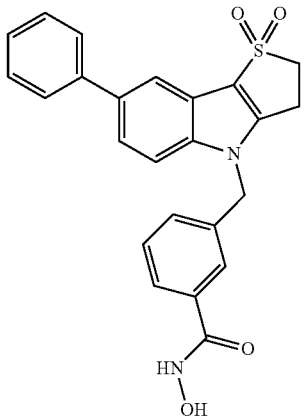 [SMILES: O=C(NO)c1cccc(Cn2c3c(c4cc(-c5ccccc5)ccc42)S(=O)(=O)CC3)c1] | 33 |
| 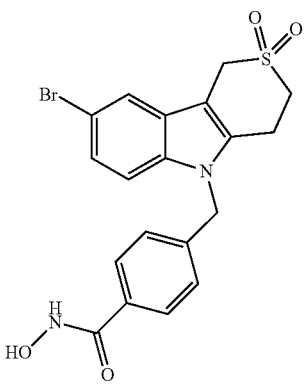 [SMILES: O=C(NO)c1ccc(Cn2c3c(c4cc(Br)ccc42)CS(=O)(=O)CC3)cc1] | 34 |

Characterization $^1$H NMR spectra were recorded at 300 MHz (JEOL ECLIPSE+) with CDCl$_3$ or d$_6$-DMSO as solvent and tetramethylsilane as internal standard. $^{13}$C NMR spectra were recorded at 75 MHz (JEOL ECLIPSE+) with CDCl$_3$ or d$_6$-DMSO as solvent and tetramethylsilane as internal standard. Mass spectra were obtained with a mass spectrometer Agilent 1100, 70 eV. IR spectra were measured with a Spectrum One FT-IR spectrophotometer. High resolution electron spray (ES) mass spectra were obtained with an Agilent Technologies 6210 series time-of-flight instrument. Melting points of crystalline compounds were measured with a Büchi 540 apparatus. The purity of all tested compounds was assessed by HRMS analysis and/or HPLC analysis, confirming a purity of ≥95%.

N-(4-Hydroxycarbamoylbenzyl)-1,2,4,9-tetrahydro-3-thia-9-azafluorene (7a)

Recrystallization from EtOH. Mp=149.6° C. $^1$H NMR (300 MHz, d$_6$-DMSO): δ 2.87 and 2.98 (2×2H, 2×t, J=5.4 Hz); 3.83 (2H, s); 5.42 (2H, s); 6.99-7.10 and 7.39-7.41 (4H and 1H, 2×m); 7.47 (1H, d×d, J=6.9, 1.4 Hz); 7.65 (2H, d, J=8.3 Hz); 9.02 (1H, s(br)); 11.14 (1H, s(br)). $^{13}$C NMR (75 MHz, d$_6$-DMSO): δ 22.8, 24.1, 25.7, 45.7, 107.0, 110.0, 118.1, 119.5, 121.7, 126.8, 126.9, 127.8, 132.4, 135.5, 135.8, 142.1, 164.5. IR (ATR, cm$^{-1}$): $v_{NH/OH}$=3201; $v_{C=O}$=1636. MS (70 eV): m/z (%) 339 (M$^+$+1, 100). HRMS (ESI) Anal. Calcd. for C$_{19}$H$_{19}$N$_2$O$_2$S, 339.1167 [M+H]$^+$. Found 339.1164.

N-(4-Hydroxycarbamoylbenzyl)-6-fluoro-1,2,4,9-tetrahydro-3-thia-9-azafluorene (7c)

Recrystallization from ethanol. Mp=194.5° C. $^1$H NMR (300 MHz, d$_6$-DMSO): δ 2.86 and 2.97 (2×2H, 2×t, J=5.7 Hz); 3.80 (2H, s); 5.42 (2H, s); 6.91 (1H, t×d, J=9.1, 2.8 Hz); 7.03 (2H, d, J=8.3 Hz); 7.26 (1H, d×d, J=9.1, 2.8 Hz); 7.41 (1H, d×d, J=9.1, 4.4 Hz); 7.65 (2H, d, J=8.3 Hz), 9.01 (1H, s(br)); 11.13 (1H, s(br)). $^{19}$F NMR (282 MHz, d$_6$-DMSO): δ (−124.75)-(−124.66) (m). $^{13}$C NMR (75 MHz, d$_6$-DMSO): δ 22.7, 24.3, 25.6, 45.9, 103.3 (d, J=23.1 Hz), 107.3 (d, J=4.6 Hz), 109.4 (d, J=26.5 Hz), 111.0 (d, J=10.4 Hz), 126.8, 127.1 (d, J=10.4 Hz), 127.8, 132.4, 132.5, 137.6, 141.9, 157.6 (d, J=230.7 Hz), 164.5. IR (ATR, cm$^{-1}$): $v_{NH/OH}$=3224; $v_{C=O}$=1613. MS (70 eV): m/z (%) 355 (M$^-$−1, 100). HRMS (ESI) Anal. Calcd. for C$_{19}$H$_{16}$FN$_2$O$_2$S, 355.0922 [M−H]$^-$. Found 355.0924.

N-(4-Hydroxycarbamoylbenzyl)-1,2,4,9-tetrahydro-3-thia-9-azafluorene-3,3-dioxide (10a)

Recrystallization from EtOH. Mp=200.2° C. $^1$H NMR (300 MHz, d$_6$-DMSO): δ 3.21 and 3.50 (2×2H, 2×t, J=6.1 Hz); 4.49 (2H, s); 5.47 (2H, s); 7.04-7.16 (4H, m); 7.45 (1H, d, J=8.3 Hz); 7.49 (1H, d, J=7.7 Hz); 7.66 (2H, d, J=8.2 Hz); 9.01 (1H, s(br)); 11.15 (1H, s(br)). $^{13}$C NMR (75 MHz, d$_6$-DMSO): δ 22.5, 46.1, 46.8, 48.6, 102.9, 110.5, 118.3, 120.1, 122.5, 126.7, 126.9, 127.9, 131.6, 132.5, 137.1, 141.7, 164.5. IR (ATR, cm$^{-1}$): $v_{NH/OH}$=3192; $v_{C=O}$=1613; $v_{S=O}$=1126, 1114. MS (70 eV): m/z (%) 371 (M$^+$+1, 100). HRMS (ESI) Anal. Calcd. for C$_{19}$H$_{19}$N$_2$O$_4$S, 371.1066 [M+H]$^+$. Found 371.1062.

N-(4-Hydroxycarbamoylbenzyl)-6-fluoro-1,2,4,9-tetrahydro-3-thia-9-azafluorene-3,3-dioxide (10c)

Recrystallization from EtOH. Mp=170.0° C. $^1$H NMR (300 MHz, d$_6$-DMSO): δ 3.19 and 3.49 (2×2H, 2×t, J=6.1 Hz); 4.46 (2H, s); 5.47 (2H, s); 6.97 (1H, t×d, J=9.1, 2.8 Hz); 7.06 (2H, d, J=8.3 Hz); 7.30 (1H, d×d, J=9.6, 2.8 Hz); 7.46 (1H, d×d, J=9.1, 4.4 Hz); 7.65 (2H, d, J=8.3 Hz), 9.01 (1H, s(br)); 11.14 (1H, s(br)). $^{19}$F NMR (282 MHz, d$_6$-DMSO): δ (−123.94)-(−123.85) (m). $^{13}$C NMR (75 MHz, d$_6$-DMSO): δ 22.6, 46.3, 46.7, 48.4, 103.1 (d, J=4.6 Hz), 103.5 (d, J=24.2 Hz), 110.4 (d, J=25.4 Hz), 111.6 (d, J=9.3 Hz), 126.9, 127.0 (d, J=12.7 Hz), 127.9, 132.5, 133.7, 133.8, 141.5, 157.8 (d, J=233.0 Hz), 164.4. IR (ATR, cm$^{-1}$): $v_{NH/OH}$=3200; $v_{C=O}$=1619; $v_{S=O}$=1146, 1123. MS (70 eV): m/z (%) 387 (M$^-$−1, 100). HRMS (ESI) Anal. Calcd. for C$_{19}$H$_{16}$FN$_2$O$_4$S, 387.0820 [M−H]$^-$. Found 387.0824.

Ligand Docking

Figure 1B:
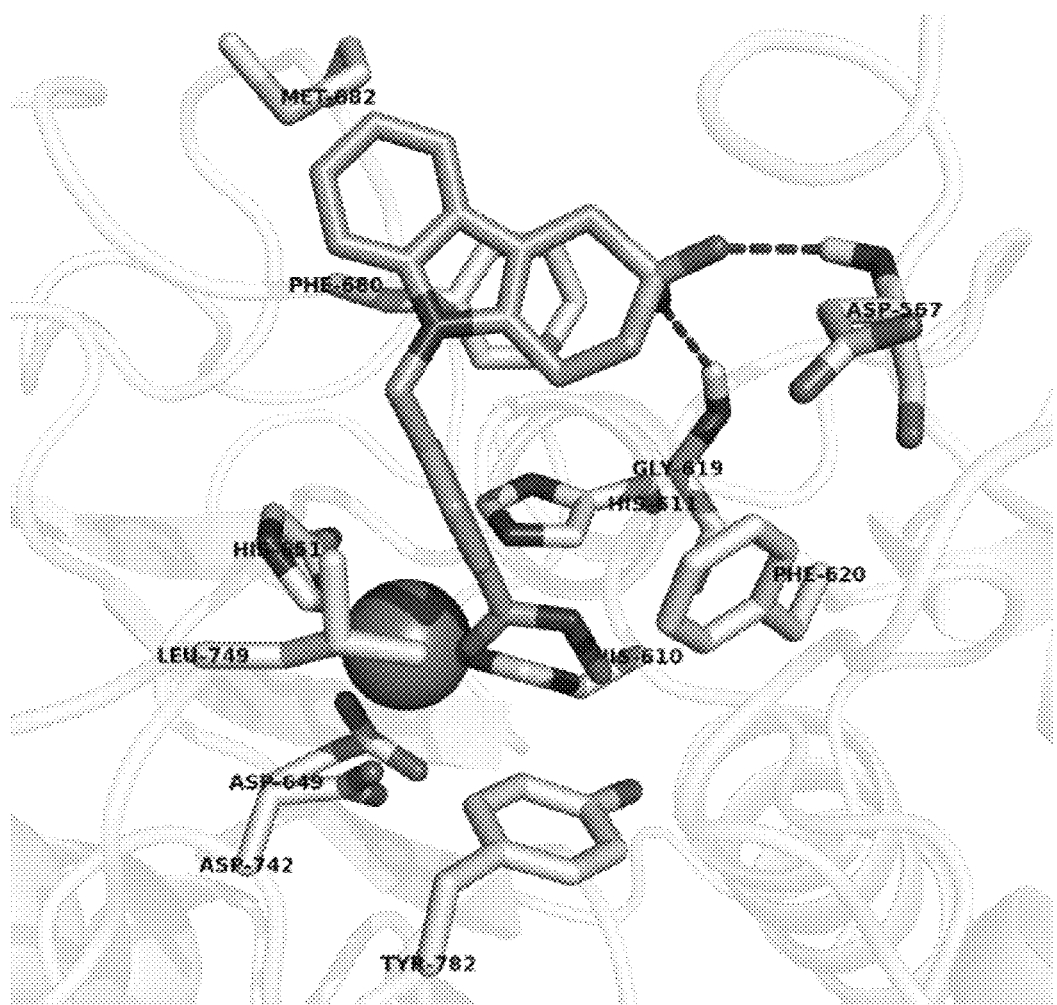
FIG. 1B: Depicts additional interactions generated by the oxidation of the sulfur atom in docking of compound 10A in the active site of HDAC6.

The binding of various ligands in the enzyme's active site was evaluated by means of automated docking. Since the crystal structure of HDAC6 is not available, a homology model was first generated following the example of Kozikowski[10] using the structure of HDAC isozymes as a template. Compounds that do not carry a methoxy group on their linker (7a, 7c, 10a and 10c) were found to fit perfectly in the active site of HDAC6 (FIG. 1). In that case, the linker is positioned in the tubular access channel, with the carbonyl group of the hydroxamate moiety within chelating distance from the zinc ion at the bottom of the pocket. As the linker fills the access channel almost completely, very little space is left to accommodate a (bulky) substituent such as a methoxy group (FIG. 1a), which is in line with previous studies in that respect. In contrast, modifications of the tricyclic cap group do not seem to influence the binding mode very much, since the conformation and orientation of compounds 7a, 7c, 10a and 10c is nearly identical. However, oxidation of the sulfur atom might generate additional interactions with the enzyme in the form of hydrogen bonds between the introduced oxygen atoms and the backbone nitrogen of residues Asp567 and Gly619 (FIG. 1b). The latter observation provided an interesting motive to experimentally assess the HDAC6 inhibitory activity of Tubastatin A analogues in which the NMe moiety is replaced by a sulfone unit.

Biological Evaluation

In the in vitro pharmacology studies of novel hydroxamic acids 7a-d and 10a-d with regard to their HDAC1 and HDAC6 inhibitory activity revealed an interesting potency of these compounds as HDAC6 inhibitors (Table 2). In particular, hydroxamic acids 7a, 7c, 10a and 10c showed complete inhibition at a test concentration of 10 μM, and also compounds 10b and 10d exhibited a good profile with an inhibition of 73% and 75%, respectively. In addition, these results pointed to a selectivity of the test compounds toward HDAC6 inhibition, with HDAC1 inhibition percentages ranging from 0% to a maximum of 53%. Furthermore, these data also indicate a detrimental effect of the introduction of a methoxy group in the linker moiety on the bioactivity (compounds 7b,d and 10b,d), as indicated by homology modeling. HDAC1 and HDAC6 were chosen for activity comparison in this preliminary test, as these two enzymes have a diverse phylogeny and are members of separate deacetylase classes.

TABLE 2

% inhibition of control values with regard to HDAC1 and HDAC6 inhibitory activity[a,b]

| Compound | % inhibition HDAC1 | % inhibition HDAC6 |
|---|---|---|
| 7a | 26 | 99 |
| 7b | 0 | 38 |
| 7c | 17 | 99 |
| 7d | 0 | 51 |
| 10a | 51 | 99 |
| 10b | 2 | 73 |
| 10c | 53 | 99 |
| 10d | 8 | 75 |

[a]Test concentration: 10 μM;
[b]Mean value of two screening sessions

The most promising molecules, i.e., those compounds showing an inhibition of >70%, were then selected for determination of their $IC_{50}$ values with respect to HDAC6 inhibition (Table 3). These assessments confirmed the presumption that molecules bearing a methoxy-substituted linker exhibit lower—but still moderate—activities, exemplified by compounds 10b and 10d (with $IC_{50}$ values of 2.0 and 1.3 μM, respectively). Furthermore, sulfur oxidation indeed seems to be beneficial for bioactivity, as sulfones 10a and 10c show even more potent HDAC6 inhibition as compared to sulfides 7a and 7c. Overall, four compounds (7a, 7c, 10a and 10c) can be considered as preferred compounds. Sulfides 7a and 7c (with $IC_{50}$ values of 15 and 22 nM, respectively) display HDAC6 inhibitory activities similar to the reference compound Trichostatin A and to Tubastatin A, but sulfones 10a and 10c are even more potent than sulfides 7a and 7c with $IC_{50}$ values of 1.9 and 3.7 nM, respectively.

TABLE 3

$IC_{50}$ values for HDAC6 inhibition[a]

| Compound | $IC_{50}$ (μM) |
|---|---|
| 7a | 0.015 |
| 7c | 0.022 |
| 10a | 0.0019 |
| 10b | 2.0 |
| 10c | 0.0037 |
| 10d | 1.3 |

[a]Reference compound: Trichostatin A ($IC_{50}$ = 0.012 μM)

Finally, the HDAC inhibition selectivity of the two most active compounds 10a and 10c against the other HDAC isoform classes was assessed and, to that end, a class I (HDAC1), a class IIa (HDAC4), a class IIb (HDAC6) and a class IV (HDAC11) isozyme was selected. Considering the fact that Tubastatin A has over 1000-fold selectivity against all HDAC isozymes except for HDAC8, where it has only a 57-fold selectivity, the HDAC8 inhibitory activity of compounds 10a and 10c was also evaluated.

TABLE 4

Comparison of HDAC selectivity

| Compound | HDAC1 $IC_{50}$ (μM)[a] | HDAC4 $IC_{50}$ (μM)[a] | HDAC6 $IC_{50}$ (μM) | HDAC8 $IC_{50}$ (μM)[a] | HDAC11 $IC_{50}$ (μM)[b] |
|---|---|---|---|---|---|
| 7c | 21 | 1.5 | 0.022 | 2.8 | 9.7 |
| 10a | 11 | 1.6 | 0.0019 | 1.7 | NC |
| 10c | 12 | 1.9 | 0.0037 | 0.93 | NC |

[a]Reference compound: Trichostatin A
[b]Reference compound: Scriptaid
NC = Not Calculable (concentration-response curve shows less than 25% effect at the highest validated testing concentration)

The data in Table 4 point to a good to excellent HDAC6 selectivity of hydroxamic acids 7c, 10a and 10c. The HDAC 11 inhibitory effect of 10a,c appeared to be very low and no $IC_{50}$ values could be obtained. Furthermore, a 5789-fold and 3243-fold selectivity against HDAC1 was determined for compounds 10a and 10c, respectively, which substantially exceeds the selectivity of Tubastatin A (1093-fold selectivity).[10] In addition, also a high HDAC6 versus HDAC4 selectivity was observed for sulfones 10a and 10c (842- and 513-fold, respectively). Finally, it is interesting to note that these compounds show a good HDAC6 versus HDAC8 selectivity, and sulfide 7c (127-fold), sulfone 10a (895-fold) and sulfone 10c (251-fold) exhibited a considerably higher selectivity in that respect as compared to Tubastatin A (57-fold).[10]

In Table 5, a comparison is made between the new compounds 10a and 10c (designated as Tubathian A and Tubathian B, respectively) and the known HDAC6 inhibitors Tubastatin A and Trichostatin A. From this Table it is clear that compounds 10a and 10c are more active and more selective (HDAC6 vs HDAC1) as compared to the known compounds.

TABLE 5

HDAC1 vs. HDAC6 selectivity

| Compound | HDAC1 IC$_{50}$ (µM) | HDAC6 IC$_{50}$ (µM) | Selectivity[a] |
|---|---|---|---|
| 10a (Tubathian A) | 11 | 0.0019 | 5789 |
| 10c (Tubathian B) | 12 | 0.0037 | 3243 |
| Tubastatin A | 16.4 | 0.015 | 1093 |
| Trichostatin A | 0.016 | 0.012 | 1.3 |

[a]Selectivity = IC$_{50}$ (HDAC1)/IC$_{50}$ (HDAC6)

The structure-activity relationship insights provided by ligand docking were corroborated by the experimental results listed in Tables 2-4. These data show that decoration of the N-(4-hydroxycarbamoylbenzyl)-1,2,4,9-tetrahydro-3-thia-9-azafluorene scaffold at the linker unit (in casu by a methoxy group) is unfavorable for HDAC6 inhibitory activity. On the other hand, introduction of a substituent (in casu a fluoro atom) at the cap group did not appear to have a significant effect on the activity profile. It should also be noted that replacement of the tertiary amine functionality (NMe moiety) in the tetrahydropyrido[4,3-b]indole core structure of Tubastatin A by a sulfide unit results in compounds with a comparable HDAC6 inhibitory activity (at least as concerns the IC$_{50}$ value), whereas replacement by a sulfone moiety (SO$_2$) affords even more potent HDAC6 inhibitors. The in silico observed occurrence of hydrogen bonds between the introduced oxygen atoms and the backbone nitrogen atom of residues Asp567 and Gly619 can account for the higher in vitro activity of these sulfone derivatives.

In addition to their promising biological potential and their straightforward and easy synthesis and purification, sulfones 10a and 10c also show an interesting profile.

In conclusion, N-(4-hydroxycarbamoylbenzyl)-1,2,4,9-tetrahydro-3-thia-9-azafluorenes were efficiently prepared and shown to be of interest as novel and selective HDAC6 inhibitors, culminating in the identification of sulfone derivatives as potent and selective HDAC6 inhibitors in the nanomolar range. In addition to the lower IC$_{50}$ values for HDAC6 inhibition, especially the considerably higher HDAC6 vs HDAC8 selectivity of the new compounds 10a and 10c as compared to Tubastatin A should be noted.

Inhibition of Proliferation

Inhibition of cell proliferation was determined using the SRB and MTT assays.

The sulforhodamine B (SRB) assay is used for cell density determination, and is based on the measurement of cellular protein content ("biomass")[12,13]. The method has been optimized for the screening of compounds for growth effects on adherent cells in a 96-well format. After an incubation period with the compound of the invention, cell monolayers (MO4 mouse fibrosarcoma cells) are fixed with 50% (wt/vol) trichloroacetic acid for 1 hour and stained with SRB for 30 min, after which the excess dye is removed by washing repeatedly with 1% (vol/vol) glacial acid. The protein-bound dye is dissolved in 10 mM Tris base solution for OD determination at 570 nm using a microplate reader. The results are linear over a 20-fold range of cell numbers, and the sensitivity is comparable to those of fluorometric methods. The method allows to test a large number of samples within a few days, and is a quantitative assay for growth inhibition by microtubule inhibitors.

Figure 2A:
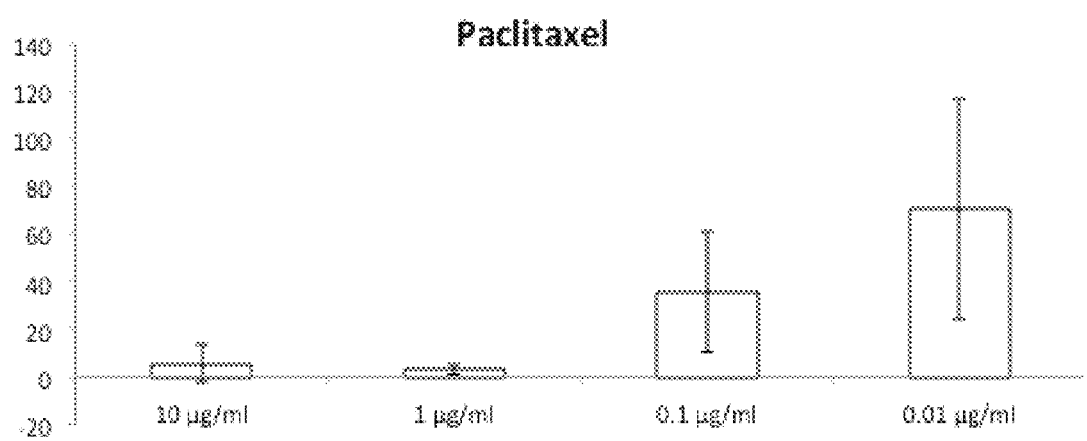
FIG. 2A: Depicts inhibition of cell proliferation with Paclitaxel as determined by the SRB assay. The mean of duplicate experiments is shown, together with error bars representing the standard deviation.
Figure 2B:
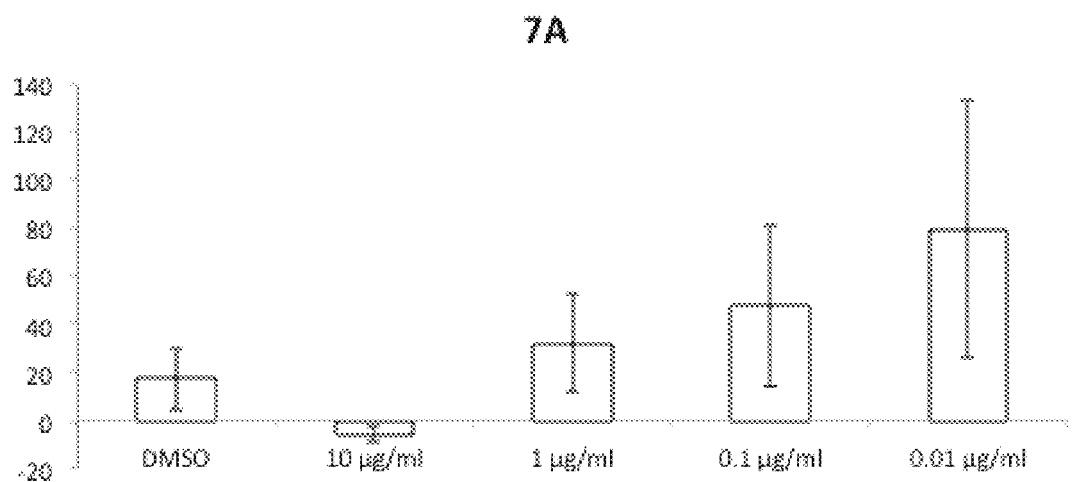
FIG. 2B: Depicts inhibition of cell proliferation with Compound 7A as determined by the SRB assay. The mean of duplicate experiments is shown, together with error bars representing the standard deviation.
Figure 2C:
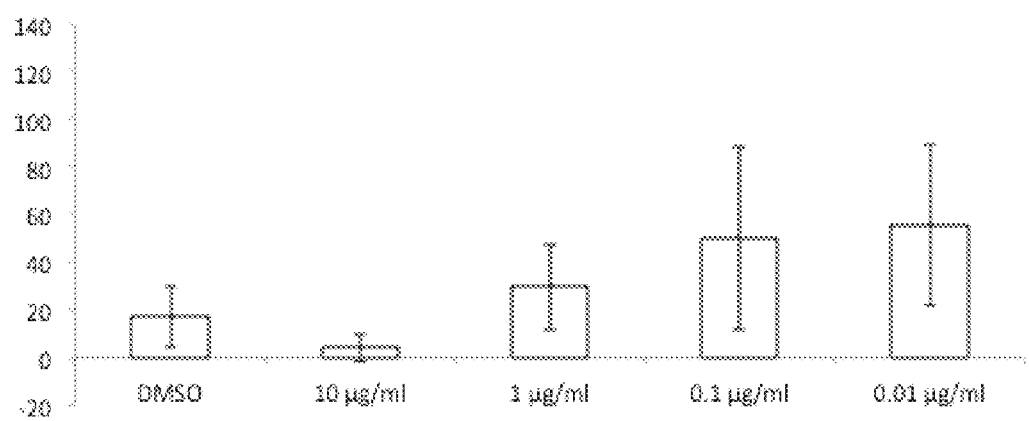
FIG. 2C: Depicts inhibition of cell proliferation with Compound 7C as determined by the SRB assay. The mean of duplicate experiments is shown, together with error bars representing the standard deviation.

Compounds 7a and 7c, as well as the positive control paclitaxel, were tested at 0.01 µg/ml, 0.1 µg/ml, 1 µg/ml and 10 µg/ml. 0.1% DMSO was used as a solvent control for the compounds of the invention. As can be seen from the results represented in FIG. 2, compounds 7a and 7c inhibit cell proliferation.

The MTT assay[14,15] is based on the reduction of MTT (3-(4,5-Dimethylthiazol-2-yl)-2,5-diphenyltetrazolium bromide, a yellow tetrazole) to purple formazan in living cells. A solubilization solution (dimethyl sulfoxide) is added to dissolve the insoluble purple formazan product into a purple solution. The absorbance of this colored solution can be quantified by measuring it at a wavelength between 500 and 600 nm by a spectrophotometer. The absorption maximum is dependent on the solvent employed. The reductions take place only when reductase enzymes are active, and therefore conversion is used as a measure of viable (living) cells. When the amount of purple formazan produced by cells treated with an agent is compared with the amount of formazan produced by untreated control cells, the effectiveness of the agent in causing death or in changing the metabolism of cells can be deduced through the production of a dose-response curve.

Figure 3A:
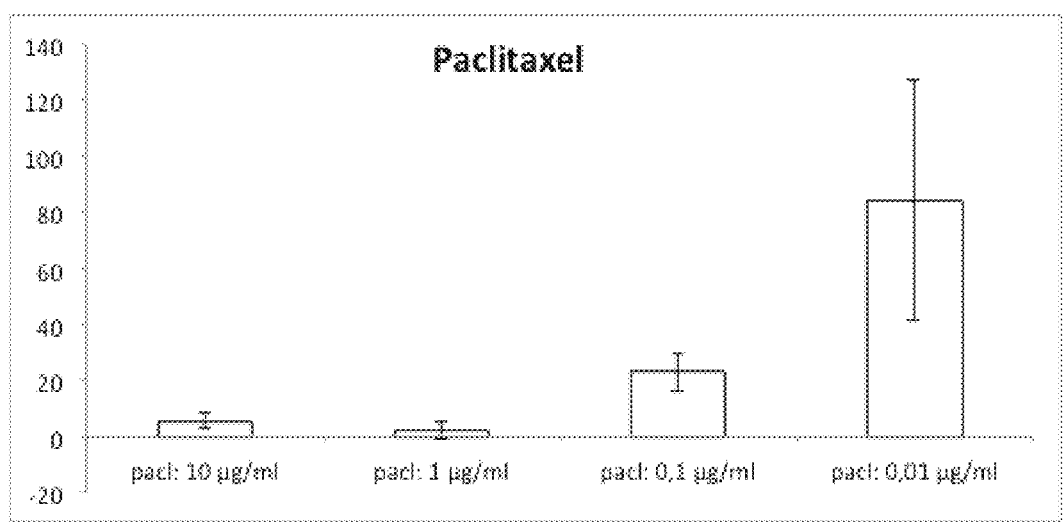
FIG. 3A: Depicts inhibition of cell proliferation with Paclitaxel as determined by the MTT assay. The mean of duplicate experiments is shown, together with error bars representing the standard deviation.
Figure 3B:
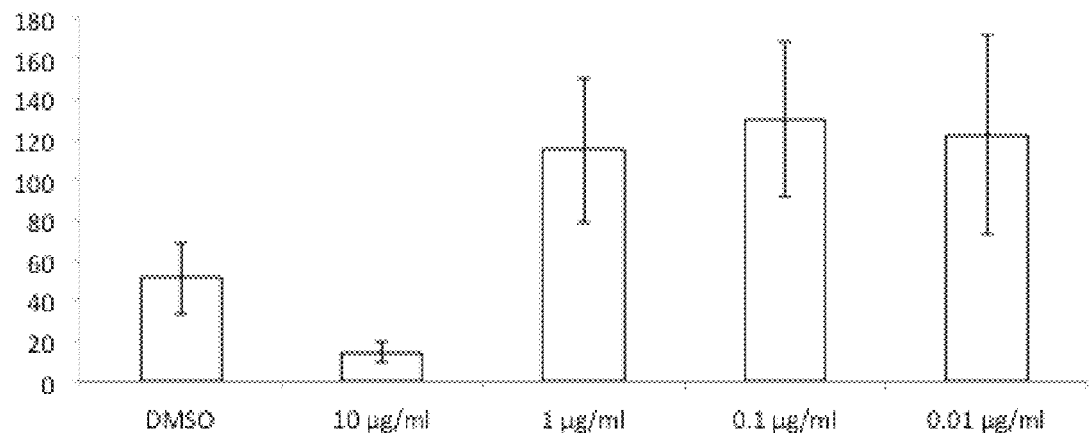
FIG. 3B: Depicts inhibition of cell proliferation with Compound 7A as determined by the MTT assay. The mean of duplicate experiments is shown, together with error bars representing the standard deviation.
Figure 3C:
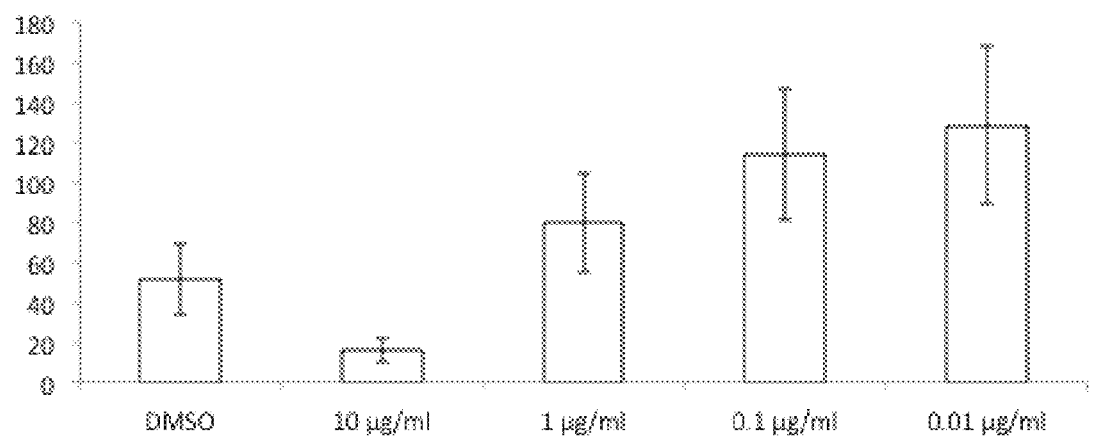
FIG. 3C: Depicts inhibition of cell proliferation with Compound 7C as determined by the MTT assay. The mean of duplicate experiments is shown, together with error bars representing the standard deviation.

Compounds 7a and 7c, as well as the positive control paclitaxel, were tested at 0.01 µg/ml, 0.1 µg/ml, 1 µg/ml and 10 µg/ml. 0.1% DMSO was used as a solvent control for the compounds of the invention. The results, represented in FIG. 3, confirm the inhibition of cell proliferation exerted by compounds 7a and 7c.

Inhibition of Invasion

To determine the effect of the compounds of the invention on invasion, compound 7c was tested in the collagen invasion assay as described by De Wever et al. (2010)[16]. Tissue invasion requires infiltration into an extracellular matrix (ECM) dominated by networks of collagen type I. The invasion model consists of native, acid-extracted rat tail collagen type I containing nonhelical telopeptides situated at the N- and C-terminal ends. These telopeptides play an important role in intermolecular covalent cross-links necessary for a gel architecture presenting itself as a structural barrier to cancer cell traffic. Collagen type I solution was prepared with a final concentration of 1 mg ml$^{-1}$ collagen type I by mixing the following pre-cooled (stored at 4° C.) components: 4 volumes collagen type I (stock is 3.49 mg ml$^{-1}$), 5 volumes of calcium- and magnesium-free Hank's balanced salt solution (CMF-HBSS), 1 volume of minimal essential medium (MEM) (10×), 1 volume of 0.25 M NaHCO$_3$, 2.65 volumes of standard medium and 0.3 volumes of 1M NaOH to make the solution alkaline. The collagen type I solution was gently poured into the wells of a 6-well plate. The experimental set-up was placed at 37° C. in a humidified atmosphere with 10% CO2 in air for at least 1 h. After gelification, a cell suspension of MDA MB 231 human mammary adenocarcinoma cells was added on top of the collagen gels and incubated for 24 hours. Invasion of cells was observed in the transparent 3D collagen gels by phase contrast microscopy as cells with extensions penetrating into the collagen gel. Invasion is calculated as the percentage of invading cells per high powered field and is expressed as the mean and standard deviation.

Figure 4:
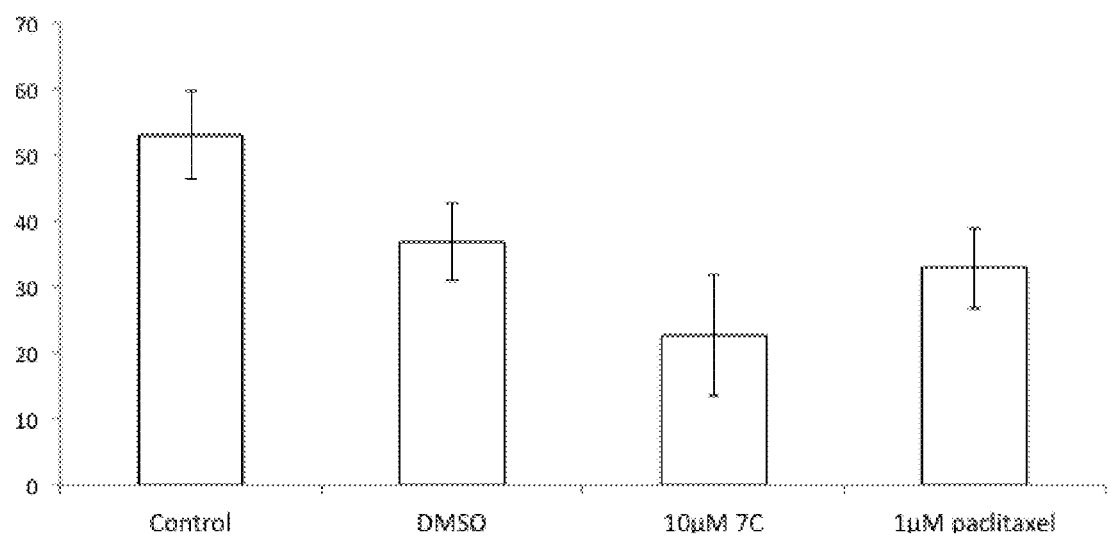
FIG. 4: Depicts inhibition of invasion by compound 7C or paclitaxel. The mean percentage of invasion of 10 measurements is shown, together with error bars representing the standard deviation.

Compound 7c (10 µg/ml) and paclitaxel (1 µg/ml) were tested in the assay. As a control, cells in medium without additional compounds was used. The effect of the solvent of compound 7c (1% DMSO) was measured as well. As can be seen from the results, shown in FIG. 4, compound 7c inhibits invasion of the cells as compared to the solvent control. After 14 days, histology confirmed inhibition of invasion.

REFERENCES

[1] Selected reviews: (a) Dokmanovic, M.; Clarke, C.; Marks, P. A. Histone Deacetylase Inhibitors: Overview and Perspectives. Mol. Cancer Res. 2007, 5, 981-989. (b) Marks, P. A. Histone deacetylase inhibitors: A chemical genetics approach to understanding cellular functions. BBA-Gene Regul. Mech. 2010, 1799, 717-725. (c) Kim, H. J.; Bae, S. C. Histone deacetylase inhibitors: molecular mechanisms of action and clinical trials as anti-cancer drugs. Am. J. Transl. Res. 2011, 3, 166-179.

[2] Selected reviews: (a) Bolden, J. E.; Peart, M. J.; Johnstone, R. W. Anticancer activities of histone deacetylase inhibitors. Nat. Rev. Drug Discov. 2006, 5, 769-784. (b) Marcotullio, L. D.; Canettieri, G.; Infante, P.; Greco, A.; Gulino, A. Protected from the inside: Endogenous histone deacetylase inhibitors and the road to cancer. Biochim. Biophys. Acta 2011, 1815, 241-252. (c) Shein, N. A.; Shohami, E. Histone Deacetylase Inhibitors as Therapeutic Agents for Acute Central Nervous System Injuries. Mol. Med. 2011, 17, 448-456. (d) Kazantsev, A. G.; Thompson M. L. Therapeutic application of histone deacetylase inhibitors for central nervous system disorders. Nat. Rev. Drug Discov. 2008, 7, 854-868.

[3] De Ruijter, A. J. M.; Van Gennip, A. H.; Caron, H. N.; Kemp, S.; Van Kuilenburg, A. B. P. Histone deacetylases (HDACs): characterization of the classical HDAC family. Biochem. J. 2003, 370, 737-749.

[4] Karagiannis, T. C.; El-Osta, A. Will broad-spectrum histone deacetylase inhibitors be superseded by more specific compounds? Leukemia 2007, 21, 61-65.

[5] Thaler, F.; Minucci, S. Next generation histone deacetylase inhibitors: the answer to the search for optimized epigenetic therapies? Expert Opin. Drug Discov. 2011, 6, 393-404.

[6] (a) d'Ydewalle, C.; Bogaert, E.; Van Den Bosch, L. HDAC6 at the Intersection of Neuroprotection and Neurodegeneration. Traffic 2012, 13, 771-779. (b) Li, G.; Jiang, H.; Chang, M.; Xie, H.; Hu, L. HDAC6 α-tubulin deacetylase: A potential therapeutic target in neurodegenerative diseases. J. Neurol. Sci. 2011, 304, 1-8. (c) Aldana-Masangkay, G. I.; Sakamoto, K. M. The Role of HDAC6 in Cancer. J. Biomed. Biotechnol. 2011, 1-10. (d) Valenzuela-Fernandez, A.; Cabrero, J. R.; Serrador, J. M.; Sanchez-Madrid, F. HDAC6: a key regulator of cytoskeleton, cell migration and cell-cell interactions. Trends Cell Biol. 2008, 18, 291-297. (e) Boyault, C.; Sadoul, K.; Pabion, M.; Khochbin, S. HDAC6, at the crossroads between cytoskeleton and cell signaling by acetylation and ubiquitination. Oncogene 2007, 26, 5468-5476.

[7] (a) Kalin, J. H.; Zhang, H.; Gaudrel-Grosay, S.; Vistoli, G.; Kozikowski A. P. Chiral Mercaptoacetamides Display Enantioselective Inhibition of Histone Deacetylase 6 and Exhibit Neuroprotection in Cortical Neuron Models of Oxidative Stress. Chem. Med. Chem. 2012, 7, 425-439. (b) Suzuki, T.; Kouketsu, A.; Itoh, Y.; Hisakawa, S.; Maeda, S.; Yoshida, M.; Nakagawa, H.; Miyata, N. Highly Potent and Selective Histone Deacetylase 6 Inhibitors Designed Based on a Small-Molecular Substrate. J. Med. Chem., 2006, 49, 4809-4812. (c) Ontoria, J. M.; Altamura, S.; Di Marco, A.; Ferrigno, F.; Laufer, R.; Muraglia, E.; Palumbi, M. C.; Rowley, M.; Scarpelli, R.; Schultz-Fademrecht, C.; Serafini, S.; Steinkiihler, C.; Jones, P. Identification of Novel, Selective, and Stable Inhibitors of Class II Histone Deacetylases. Validation Studies of the Inhibition of the Enzymatic Activity of HDAC4 by Small Molecules as a Novel Approach for Cancer Therapy. J. Med. Chem., 2009, 52, 6782-6789. (d) Smil, D. V.; Manku, S.; Chanigny, Y. A.; Leit, S.; Wahhab, A.; Yan, T. P.; Fournel, M.; Maroun, C.; Li, Z.; Lemieux, A. M.; Nicolescu, A.; Rahil, J.; Lefebvre, S.; Panetta, A.; Besterman, J. M.; Deziel, R. Novel HDAC6 isoform selective chiral small molecole histone deacetylase inhibitors. Bioorg. Med. Chem. Lett. 2009, 19, 688-692. (e) Schafer, S.; Saunders, L.; Eliseeva, E.; Velena, A.; Jung, M.; Schwienhorst, A.; Strasser, A.; Dickmanns, A.; Ficner, R.; Schlimme, S.; Sippl, W.; Verdin, E.; Jung, M. Phenylalanine-containing hydroxamic acids as selective inhibitors of class IIb histone deacetylases (HDACs). Bioorg. Med. Chem. 2008, 16, 2011-2033. (f) Olsen, C. A.; Ghadiri, M. R. Discovery of Potent and Selective Histone Deacetylase Inhibitors via Focused Combinatorial Libraries of Cyclic α3β-Tetrapeptides. J. Med. Chem., 2009, 52, 7836-7846. (g) Schäfer, S.; Saunders, L.; Schlimme, S.; Valkov, V.; Wagner, J. M.; Kratz, F.; Sippl, W.; Verdin, E.; Jung, M. Pyridylalanine-Containing Hydroxamic Acids as Selective HDAC6 Inhibitors. ChemMedChem 2009, 4, 283-290. (h) Smil, D. V.; Manku, S.; Chantigny, Y. A.; Leit, S.; Wahhab, A.; Yan, T. P.; Fournel, M.; Maroun, C.; Li, Z. M.; Lemieux, A. M.; Nicolescu, A.; Rahil, J.; Lefebvre, S.; Panetta, A.; Besterman, J. M.; Deziel, R. Novel HDAC6 isoform selective chiral small molecule histone deacetylase inhibitors. Bioorg. Med. Chem. Lett. 2009, 19, 688-692. (i) Gupta, P. K.; Reid, R. C.; Liu, L. G.; Lucke, A. J.; Broomfield, S. A.; Andrews, M. R.; Sweet, M. J.; Fairlie, D. P. Inhibitors selective for HDAC6 in enzymes and cells. Bioorg. Med. Chem. Lett. 2010, 20, 7067-7070.

[8] Rivieccio, M. A.; Brochier, C.; Willis, D. E.; Walker, B. A.; D' Annibale, M. A.; McLaughlin, K.; Siddiq, A.; Kozikowski, A. P.; Jaffrey, S. R.; Twiss, J. L.; Ratan, R. R.; Langley, B. HDAC6 is a target for protection and regeneration following injury in the nervous system. Proc. Natl. Acad. Sci. USA 2009, 106, 19599-19604.

[9] Wong, J. C.; Hong, R.; Schreiber, S. L. Structural Biasing Elements for In-Cell Histone Deacetylase Paralog Selectivity. J. Am. Chem. Soc. 2003, 125, 5586-5587.

[10] Butler, K. V.; Kahn, J.; Brochier, C.; Vistoli, G.; Langley, B.; Kozikowski, A. P. Rational Design and Simple Chemistry Yield a Superior, Neuroprotective HDAC6 Inhibitor, Tubastatin A. J. Am. Chem. Soc. 2010, 132, 10842-10846.

[11] Kahn, J. H.; Butler, K. V.; Akimova, T.; Hancock, W. W.; Kozikowski, A. P. Second-generation histone deacetylase 6 inhibitors enhance the immunosuppressive effects of Foxp3+T-regulatory cells. J. Med. Chem. 2012, 55, 639-651.

[12] Skehan P, Storeng R, Scudiero D, Monks A, McMahon J, Vistiva D, Warren J. T, Bokesch H, Kenney S and Boyd M. R. New colorimetric cytotoxicity assay for anticancerdrug screening. J Natl Cancer Inst 1990, 82, 1107-1112.

[13] Papazisis K. T, Geromichalos G. D, Dimitriadis K. A and Kortsaris A. H. Optimization of the sulforhodaminbB colorimetric assay. J Immunol Methods 1997, 208, 151-158.

[14] Mosmann T. Rapid colorimetric assay for cellular growth and survival: application to proliferation and cytotoxicity assays. J Immunol Methods 1983, 65, 55-63

What is claimed is:

1. A compound of formula I, or a stereoisomer, tautomer, racemic, prodrug, salt, hydrate, or solvate thereof:

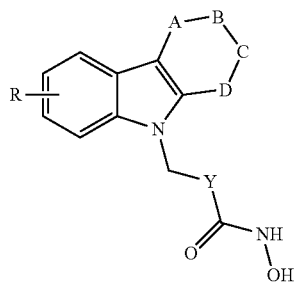

wherein:
ring

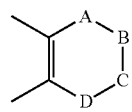

is a five- or six-membered ring wherein one of A, B, C and D is S, S=O, or SO$_2$ and the remaining are a direct bond or CH$_2$;

Y is alkylene or arylene;

R is selected from the group consisting of hydrogen, halogen, alkyl, haloalkyl, aryl, OR', SR', NR'R", and P(O)(OR')(OR"); and R' and R" are independently selected from the group consisting of H, alkyl, and aryl.

2. The compound according to claim 1, wherein ring

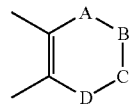

is a six-membered ring wherein one of A, B, C and D is S or SO$_2$ and the remaining are CH$_2$;

Y is arylene;

R is selected from the group consisting of hydrogen, halogen, alkyl, haloalkyl, aryl, OR', SR', NR'R", and P(O)(OR')(OR"); and R' and R" are independently selected from the group consisting of H, alkyl, and aryl.

3. The compound according to claim 1, wherein the compound has one of the formulas II-VI

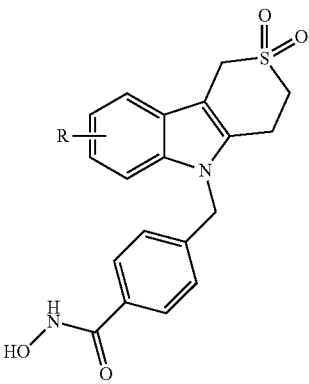

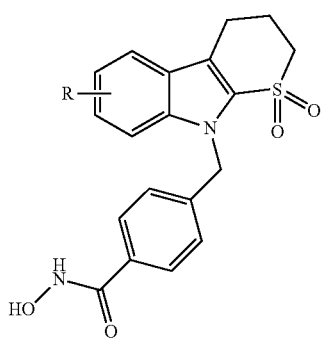

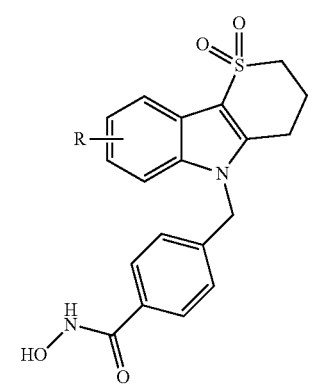

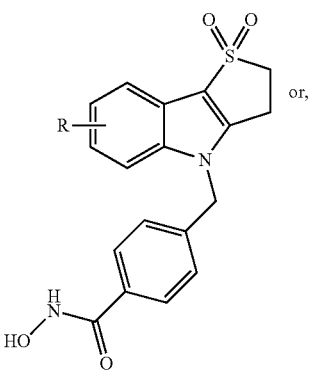

or,

VI
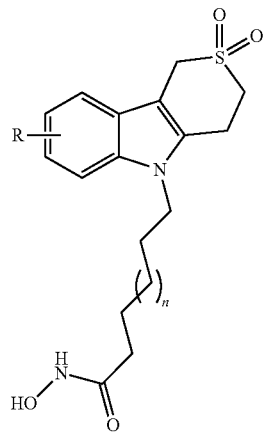
wherein R is selected from the group consisting of hydrogen, halogen, alkyl, haloalkyl, aryl, OR', SR', NR'R'', and P(O)(OR')(OR''); and
n is an integer of 0 to 10.
4. The compound according to claim 1, wherein R is hydrogen or halogen.
5. The compound according to claim 1, selected from the group consisting of
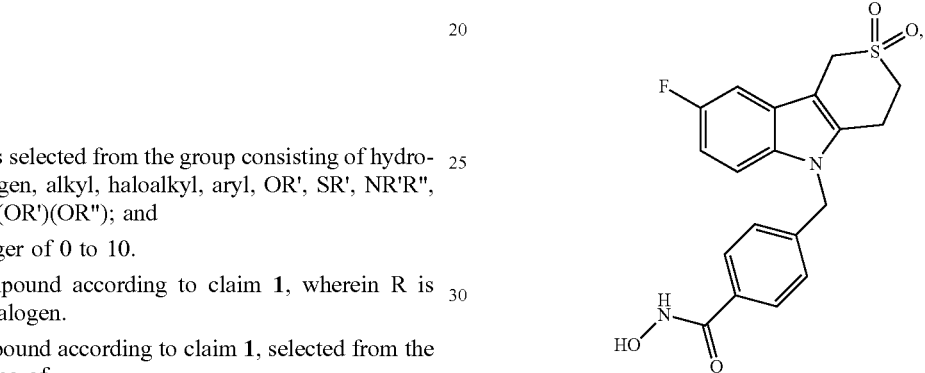
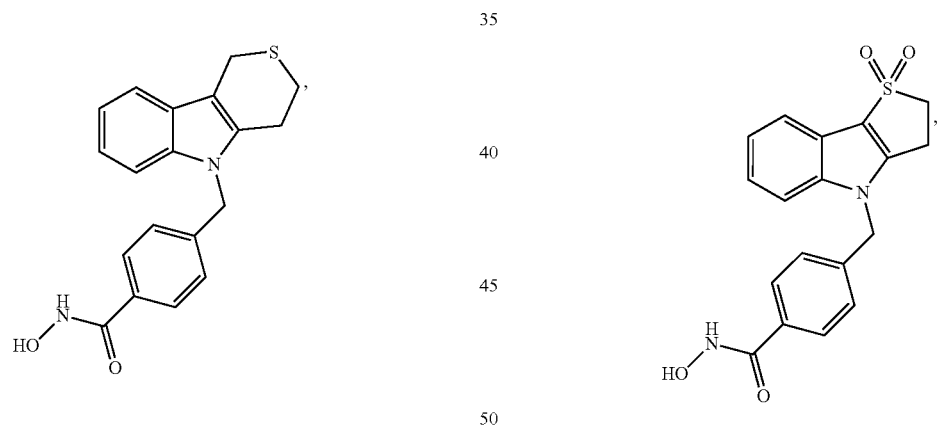
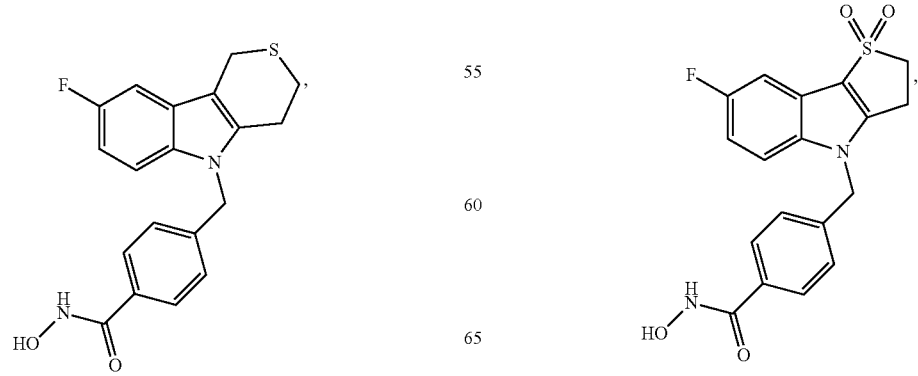

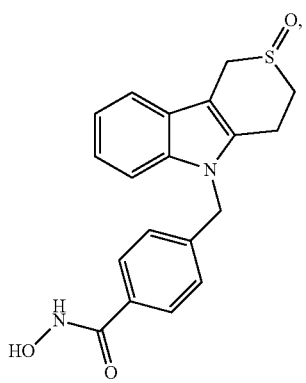

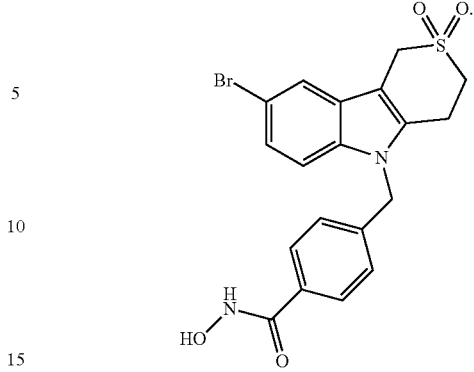

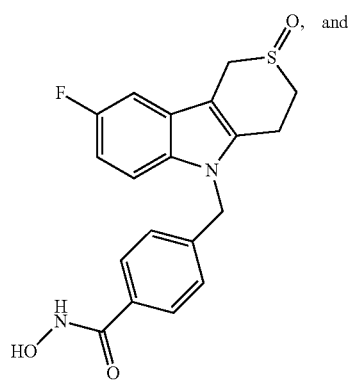

6. A composition comprising a compound according to claim 1, and one or more pharmaceutically acceptable carriers, diluents and/or excipients.

7. The composition according to claim 6, further comprising an adjuvant and/or an anticancer agent.

8. The composition according to claim 6, wherein said composition is in a form suitable for oral, parenteral or topical administration, administration by inhalation, by a skin patch, by an implant or by a suppository.

9. The compound of claim 1, wherein one of A, B, C, and D is S=O or $SO_2$ and the remaining are $CH_2$ or a direct bond.

10. A method for inhibiting a histone deacetylase (HDAC) in a subject in need thereof, said method comprising administering a compound according to claim 1 to said subject.

11. The method according to claim 10 wherein the subject has an HDAC-associated disease selected from the group consisting of a cell proliferative disease, an autoimmune disease, an inflammatory disorder, a neurodegenerative disease, a viral disease, malaria, or a combination thereof.

12. The method according to claim 10 wherein the subject has a cell proliferative disease.

13. The method according to claim 12, wherein the cell proliferative disease is cancer, or metastasis thereof.

14. A method for treating a cancer in a subject in need thereof, said method comprising administering a compound according to claim 1 to said subject.

* * * * *